(12) United States Patent
Begley et al.

(10) Patent No.: US 7,355,085 B2
(45) Date of Patent: Apr. 8, 2008

(54) PROCESS OF MAKING NAPHTHACENE FROM A PROPARGYL ALCOHOL

(75) Inventors: William J. Begley, Webster, NY (US); Manju Rajeswaran, Fairport, NY (US); Natasha Andrievsky, Webster, NY (US)

(73) Assignee: Eastman Kodak Company, Rochester, NY (US)

( * ) Notice: Subject to any disclaimer, the term of this patent is extended or adjusted under 35 U.S.C. 154(b) by 728 days.

(21) Appl. No.: 10/899,919

(22) Filed: Jul. 27, 2004

(65) Prior Publication Data

US 2006/0025618 A1 Feb. 2, 2006

(51) Int. Cl.
*C07C 1/20* (2006.01)
(52) U.S. Cl. ...................... 585/320; 585/469
(58) Field of Classification Search ............... 585/320; 595/469
See application file for complete search history.

(56) References Cited

U.S. PATENT DOCUMENTS 4,855,520 A 8/1989 Essenfeld

OTHER PUBLICATIONS

Moureu et al., C. R. Acad. Sci. (1926), vol. 182, pp. 1440-1443.
Moureu et al., Bull. de la Soc., Chim. de Fr. (1930), vol. 47, pp. 216-221.
Wittig et al., J. Fur Praktische Chemie, (1942), vol. 160, pp. 242-244.
Rigaudy et al., Tetrahedron (1977), vol. 33, pp. 767-773.
W. J. Begley, et al., "Synthesis Process", U.S. Appl. No. 10/899,825, filed herewith.
W. J. Begley, et al., "Synthesis Process", U.S. Appl. No. 10/899,821, filed herewith.

*Primary Examiner*—Thuan Dinh Dang
(74) *Attorney, Agent, or Firm*—Artthur E. Kluegel

(57) ABSTRACT

A process for synthesizing a single isomer of a naphthacene compound comprises the steps of:
(a) reacting a symmetrically substituted 1,1-diarylpropargyl alcohol compound with a reagent capable of forming a leaving group to form a reaction mixture containing a intermediate;
and then
(b) heating the intermediate in the presence of a solvent and in the absence of any oxidizing agent to form a single naphthacene compound.

65 Claims, No Drawings

PROCESS OF MAKING NAPHTHACENE FROM A PROPARGYL ALCOHOL

CROSS REFERENCE TO RELATED APPLICATIONS

This application is one of three applications cofiled under Ser. Nos. 10/899,825, 10/899,919, and 10/899,821.

FIELD OF THE INVENTION

This invention relates to the synthesis of naphthacene compounds bearing at least two aryl groups using a symmetrically substituted benzophenone and a mono-substituted acetylene compounds to form symmetrically substituted 1,1-diarylpropargyl alcohols, which are further reacted to give a single naphthacene compound.

BACKGROUND OF THE INVENTION

Organic electroluminescent (EL) devices have been known for over two decades, their performance limitations have represented a barrier to many desirable applications. In simplest form, an organic EL device is comprised of an anode for hole injection, a cathode for electron injection, and an organic medium sandwiched between these electrodes to support charge recombination that yields emission of light. These devices are also commonly referred to as organic light-emitting diodes, or OLEDs.

The organic layers in these devices are usually composed of a polycyclic aromatic hydrocarbon. Substituted naphthacenes is one class of fluorescent materials useful in the manufacture of EL devices. The naphthacene known as rubrene, or 5,6,11,12-tetraphenylnaphthacene, is commercially available and can be prepared by reacting 1,1,3-triphenylpropargyl alcohol with thionyl chloride and heating the resulting product in the presence of an organic hindered amine base. However, the yields of rubrene prepared in this manner are usually low, not reproducible and contain impurities. Rubrene, prepared in this manner, must be subjected to extensive purification techniques to render it sufficiently pure to be useful in EL devices. In addition, when substituents are present in the starting propargyl alcohol, formation of naphthacene isomers occurs.

Because rubrene and its derivatives are very prone to photo-oxidation, the normal purification techniques of re-crystallization and chromatography are not easily applied to the purification of the crude material from the reaction. Precautions have to be taken to eliminate the presence of oxygen or light. Impurities and isomers from the preparation procedure, and also the photo-oxidation products or endoperoxides as they are known, that contaminate rubrene or other naphthacene derivatives give rise to EL devices with unacceptable performance. Even very small amounts of impurities, such as 1% or less, can cause significant problems in EL devices.

Moureu et al., C.R. Acad. Sci. (1926), Vol. 182, 1440; Moureu et al., Bull. de la Soc. Chim. de Fr. (1930), Vol. 47, 216; Wittig et al., J. Fur Praktische Chemie, (1942), Vol. 160, 242; Rigaudy et al., Tetrahedron (1977), Vol. 33, 767; and Essenfeld, U.S. Pat. No. 4,855,520 refer to the preparation of rubrene in yields ranging from 20-50% and employ different techniques to purify the material.

Moureu et al., in C.R. Acad. Sci. (1926), Vol. 182, p. 1441, describes the preparation of rubrene from 3-chloro-1,3,3-triphenylpropyne by heating this material from 71° C. to 120° C. in the absence of solvent. The purification and removal of impurities from the crude material requires an involved procedure of treating with different solvents.

Moureu et al., Bull. de la Soc. Chim. de Fr. (1930), Vol. 47, p. 217-220 does not describes the preparation of rubrene but describes the influence of factors such as dilution and catalysts on the formation from 3-chloro-1,3,3-triphenylpropyne. The conclusion is that the best procedure for the preparation of rubrene from 3-chloro-1,3,3-triphenylpropyne is by heating the material in the absence of solvent. The purification and removal of impurities from the crude material requires a very involved procedure of treating with different solvents including the high boiling solvent, naphthalene.

Wittig et al., J. Fur Praktische Chemie, (1942), Vol. 160, p. 244 also describes the preparation of rubrene from 3-chloro-1,3,3-triphenylpropyne by heating this material under vacuum to 120° C. in the absence of solvent. Again, the purification and removal of impurities from the crude material requires an involved procedure of treating with different solvents.

Rigaudy et al., Tetrahedron (1977), Vol. 33, p. 773, describes the preparation of rubrene from a cyclobutane derivative.

Essenfeld, in U.S. Pat. No. 4,855,520 describes a long and involved procedure for the preparation of naphthacenes in the presence of a hindered amine base, and reports a yield of 37%. The procedure calls for the use of several different solvents. Careful removal of the initial low boiling solvent from the reaction mixture is followed by the careful addition of a second solvent with a high boiling point. Hindered amine bases are disadvantageous in manufacturing processes because they are oftentimes expensive and not environmentally safe, requiring special handling and disposal procedures. Furthermore, when substituents are introduced into the procedure of that described by Essenfeld, naphthacene isomers are formed. Isomer formation is undesirable in materials to be employed in EL devices because each isomer will have different chemical and physical properties and would have to be separated into single components before they could be used in the EL devices. Separation into single isomers or components requires additional effort and is often difficult.

The stability and luminance performance of these fluorescent materials in EL devices in general, tends to improve when fabricated from single materials with high purity. There is a continuing need in the EL industry for new, short, environmentally friendly and simple procedures for the preparation of single isomer, high purity naphthacenes. Devices fabricated from naphthacenes with low purity give poorer performing EL devices and limit the applications of these EL devices.

The problem to be solved therefore is to provide a simple procedure that would yield high purity single naphthacene compounds. Such procedures should require minimum exposure to light and oxygen and which could be applied to the preparation of naphthacenes with a variety of substituents.

SUMMARY OF THE INVENTION

The invention provides a process for synthesizing a single isomer of a naphthacene compound comprising the steps of:
(a) reacting a symmetrically substituted 1,1-diarylpropargyl alcohol compound with a reagent capable of forming a leaving group to form a reaction mixture containing a intermediate;
and then
(b) heating the intermediate in the presence of a solvent and in the absence of any oxidizing agent to form a single naphthacene compound.

The process provides a simple and rapid way to prepare single isomers of naphthacene derivatives in good yield with high purity useful for OLED devices.

DETAILED DESCRIPTION OF THE INVENTION

The process of the invention is generally as described above. It is a process for synthesizing single isomers of symmetrically substituted naphthacene compounds containing at least two aryl groups comprising a step (a), employing a symmetrically substituted 1,1-diarylpropargyl alcohol and converting the alcohol group of said symmetrically substituted 1,1-diarylpropargyl alcohol into a leaving group to give a intermediate and step (b), further reacting said intermediate with the leaving group under heating conditions in the absence of either light or oxygen and in the presence of a solvent, into a single symmetrically substituted naphthacene compound.

The type, number and location of substituent groups on the aforementioned 1,1-diarylpropargyl alcohol is key to the current invention. The term symmetrically substituted is used to indicate that the type of substituent group as well as the number of substituents and their location, are identical on both the aryl groups of said 1,1-diarylpropargyl alcohol. If the substituents on either of the aryl groups of the 1,1-diarylpropargyl alcohol are different, as in U.S. Pat. No. 4,855,520, then several isomers of the naphthacene compound are formed.

Optionally, an acid scavenger can be employed in step (a) of the invention and can be an amine base or an inorganic base. The acid scavenger employed may be any material, which is known to be useful for this purpose. Suitable scavengers useful in step (a) are primary, secondary or tertiary amine bases. Particularly useful amine bases are triethylamine, pyridine, 1,8-diazobicyclo[5,4,0]undeca-7-ene, diisopropylethylamine, tetramethylethylenediamine and the like. In addition to amine bases, other useful acid scavengers are inorganic bases, such as the basic salts of metals or non-metals and in particular, the basic salts of groups 1 and 2 of the periodic table. Specifically, metal and non-metal carbonates are other examples of useful inorganic scavengers. Examples of these inorganic bases useful in the invention are $Li_2CO_3$, $Na_2CO_3$, $K_2CO_3$, $Rb_2CO_3$, $Cs_2CO_3$, $MgCO_3$, $CaCO_3$, $BaCO_3$, NaOAc also known as sodium acetate, and $(NH_4)_2CO_3$ also known as ammonium carbonate, and the like but are not limited to these examples.

Optionally, a base can be employed in step (b) of the invention and can be any amine or inorganic base. Useful amine bases include primary, secondary or tertiary amines including hindered amine bases. Particularly useful amine bases are triethylamine, pyridine, 1,8-diazobicyclo[5,4,0]undeca-7-ene, diisopropylethylamine, tetramethylethylenediamine, collidine and lutidine bases and other like organic bases. Inorganic bases useful in step (b) of the invention are basic salts of metals and non-metals. In particular, the basic salts of groups 1 and 2 of the periodic table. Specifically, metal and non-metal carbonates are other examples of useful inorganic bases. Examples of these inorganic bases useful in step (b) of the invention are $Li_2CO_3$, $Na_2CO_3$, $K_2CO_3$, $Rb_2CO_3$, $Cs_2CO_3$, $MgCO_3$, $CaCO_3$, $BaCO_3$, NaOAc also known as sodium acetate, and $(NH_4)_2CO_3$ also known as ammonium carbonate and the like, but are not limited to these examples.

The solvents employed in steps (a) and (b) may be the same, or different for each step. Useful solvents for step (a) are diethyl ether, methylene chloride, tetrahydrofuran, ethyl acetate and the like. Particularly useful solvents for step (a) are solvents with low boiling points, which can be easily removed if they are to be replaced by a second solvent in step (b). Useful solvents for step (b) are benzene, toluene, xylene and xylene mixtures. Particularly useful solvents for step (b) are solvents with high boiling points, which are needed for the high temperatures necessary to get the reaction of step (b) to proceed at a reasonable rate. Alternatively, the high boiling point solvent described above for step (b) can be employed in both steps (a) and (b) eliminating the need to replace the low boiling point solvent of step (a).

Temperatures useful in steps (a) and (b) are any temperatures suitable to bring about first, the reaction of step (a) and then the second reaction of step (b). When the reagent capable of forming the leaving group in step (a) is reactive, the temperature for reaction to occur is normally low and usually falls in the range of from $-30°$ C. to $+30°$ C. but is not limited to this range. A particularly useful temperature range for step (a) is from $0°$ C. to $+20°$ C.

The temperature range required for step (b) is from $+30°$ C. to $+180°$ C. but is not limited to this range. A particularly useful temperature range for step (b) is from $+70°$ C. to $+120°$ C.

To prevent photo-oxidation of the naphthacene compound the reaction is conducted under either an inert atmosphere or in the absence of light. Most conveniently, both oxygen and light are excluded from the reaction. Oxygen present in air is considered an oxidizing agent when the reaction is exposed to light which causes photo-oxidation. To prevent photo-oxidation, an atmosphere of nitrogen is most conveniently employed in both steps (a) and (b).

The reaction time for step (a) is from 5 minutes to 3 hours but most conveniently from 10 minutes to 30 minutes, while the reaction time for step (b) is from 1 to 48 hours, but most conveniently complete in 1 to 8 hours and usually in 4 to 5 hours.

The reagents used in the present invention to form the leaving group X of the propargyl alcohol in step (a), can be any reagent used to form leaving groups with alcohols, particularly propargyl alcohols. The hydrogen of the alcohol can be replaced to give oxygen based leaving groups or the complete hydroxyl group can be replaced. When the complete hydroxyl group is replaced, reagents such as thionyl chloride, thionyl bromide, phosphorous trichloride, phosphorous tribromide, phosphorous pentachloride and phosphorous oxychloride may be selected, but is not limited to this list. In these cases, the X group is Cl or Br. When just the hydrogen of the propagyl alcohol is replaced, reagents such as alkanesulfonyl halides, acyl halides and anhydrides are useful reagents but are not limited to this list. Particularly useful reagents are methanesulfonyl chloride and acetyl chloride. When methanesulfonyl chloride is the reagent, the leaving group is methanesulfonate and is represented as $CH_3SO_3$, whereas the leaving group is acetate, represented by OAc, when the reagent is acetic anhydride or acetyl chloride.

The intermediate of step (a) can be represented by the symmetrically substituted Formulae (Ia) or (Ib) as follows:

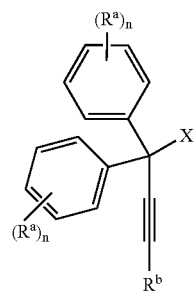

(Ia)

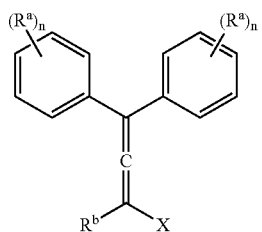

(Ib)

wherein:
the $R^a$ groups are selected from hydrogen or substituent groups;
$R^b$ is hydrogen or a substituent group;
n is selected from 0-4;
X is a leaving group; and provided that when n is 0 $R^b$ is not phenyl.

When the $R^b$ group of Formulae (Ia) and (Ib) is a heterocyclic or carbocyclic ring group then the intermediate of step (a) can be represented by Formulae (IIa) and (IIb) as follows:

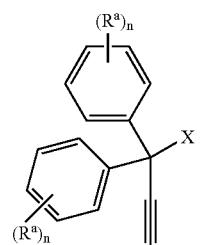

(IIa)

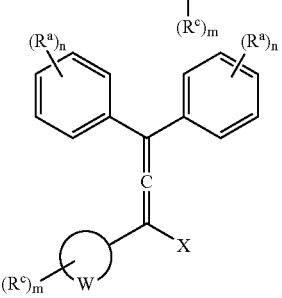

(IIb)

wherein:
the $R^a$ and $R^c$ groups are selected from hydrogen or substituent groups;
n is selected from 0-4;
m is selected from 0-5;
W represents the atoms necessary to complete a heterocyclic or carbocyclic ring group;
X is a leaving group; and provided that when W forms a phenyl group the $R^a$ and $R^c$ are not all hydrogen.

When the $R^b$ group of Formulae (Ia) and (Ib) is an aryl group then the intermediate of step (a) can be represented by Formulae (IIIa) and (IIIb) as follows:

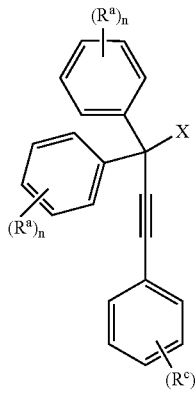

(IIIa)

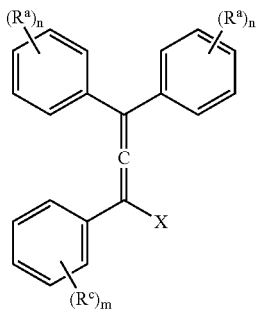

(IIIb)

wherein:

the $R^a$ groups are selected from hydrogen or substituent groups;

$R^c$ is hydrogen or a substituent group;

n is selected from 0-4;

m is selected from 0-5;

X is a leaving group; and provided that $R^a$ and $R^c$ are not all hydrogen.

The intermediate of step (a) can be represented by either the acetylenes of Formulae (Ia), (IIa) and (IIIa) or by the allenes of Formulae (Ib), (IIb) and (IIIb). It is believed that the reagent used to form the leaving group first reacts with the propargyl alcohol of step (a) to initially form the intermediates of Formulae (Ia) or (IIa) which then rearrange to the allenes of Formulae (Ib) or (IIb). During the heating in step (b) two of these allene molecules then react to form the naphthacenes. On one occasion, this has been confirmed by isolating the intermediate of step (a) and carrying out a single crystal x-ray analysis of the intermediate to determine its structure. When this allene material is heated in a high boiling point solvent, the naphthacene forms.

When the intermediate derivative of step (a) of the invention is represented by Formulae (Ia) or (Ib) then the naphthacenes of step (b) can be represented by Formulae (IVa) as follows:

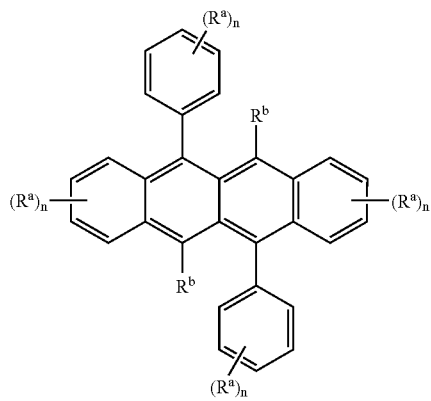

(IVa)

When $R^b$ in Formulae (Ia) or (Ib) represent a heterocyclic or carbocyclic ring group then the naphthacenes of step (b) of the invention can be represented by Formulae (IVb):

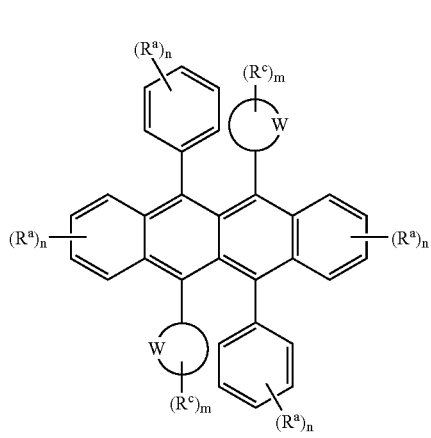

(IVb)

When W in Formulae (IIa) or (IIb) represent the atoms necessary to complete an aryl group the naphthacenes in step (b) of the invention can be represented by Formulae (IVc):

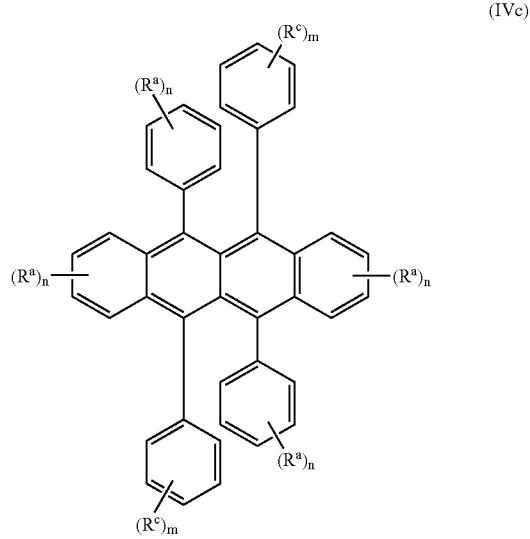

(IVc)

The substituted 1,1-diarylpropargyl alcohol materials employed in step (a) of the invention are represented by Formulae (Va), (Vb) or (Vc) as follows:

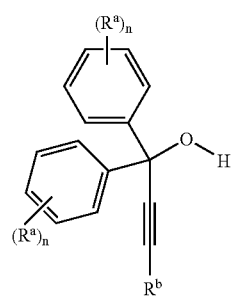

(Va)

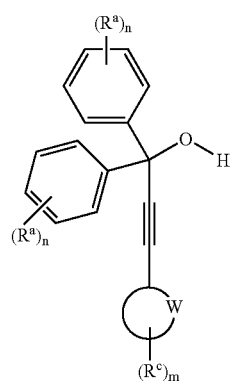

(Vb)

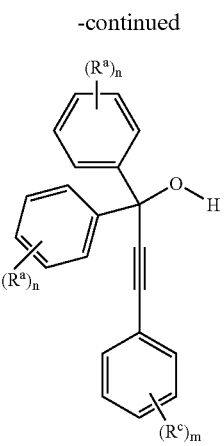

(Vc)

The term symmetrically substituted is used to indicate that the type of substituent group $R^a$, as well as the number n of $R^a$ groups and their location, are identical on both the phenyl groups bearing these groups in Formulae (Ia), (IIa), (IIIa), (Ib), (IIb) and (IIIc). In the invention, the $R^c$ groups may or may not be identical to $R^a$ in terms of substituent type, number n, and location. When the $R^a$ groups are identical, only a single naphthacene isomer is formed.

The propargyl alcohols are readily available by the addition of the anion of a mono-substituted acetylene such as a mono-arylacetylene, to a symmetrically substituted benzophenone. The anion of the mono-substituted acetylene can be prepared by the action of a strong base, such as potassium tert-butoxide, with the mono-substituted acetylene in an inert solvent such as dimethylformamide. The aforementioned benzophenone and acetylene can be suitably substituted to give various symmetrically substituted propargyl alcohols.

The R, $R^a$ and $R^b$ groups of the current invention can be selected from cyano, nitro, halogen, hydroxy, alkyl, alkenyl, alkoxy, aryl, aryloxy, acyl, oxysulfonyl, acyloxy, oxycarbonyl, carboxy, carbocyclic, heterocyclic, sulfoxide, thio, sulfamoyl, sulfonamido, sulfonyl, carbamoyl, carbonamido, ureido, and trifluoromethyl groups. Preferred compounds of the invention are obtained when R is an aryl group, and $R^a$ and $R^b$ selected from aryl or alkyl groups. The numerical value of n can be 0-4, but a preferred range is 0-3. The numerical value for m is 0-5, but a preferred range is 0-3. Particularly useful in the invention is when n is 1 and m is 0-3 and the substituents are individually located in the meta and para positions.

When $R^a$ and $R^b$ each constitute a ring, the rings can be individually carbocyclic and heterocyclic in nature. When the ring is carbocyclic a preferred ring is phenylene, which in combination with the phenyl groups in formulae (Ia)-(IVa) and (Ib)-(IVb) give a naphthalene group. Also, when $R^a$ or $R^b$ each form a heteroocyclic group the preferred heterocyclic group is furyl, imidazolyl, pyrazolyl, pyridyl, pyrrolyl, thienyl, or triazolyl.

Unless otherwise specifically stated, use of the term "substituted" or "substituent" means any group or atom other than hydrogen. Additionally, when the term "group" or "compound" is used, it means that when a group contains a substitutable hydrogen, it is also intended to encompass not only the group's unsubstituted form, but also its form further substituted with any substituent group or groups as herein mentioned, so long as the substituent does not destroy properties necessary for device utility. Suitably, a substituent group may be halogen or may be bonded to the remainder of the molecule by an atom of carbon, silicon, oxygen, nitrogen, phosphorous, sulfur, selenium, or boron. The substituent may be, for example, halogen, such as chloro, bromo or fluoro; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy)butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecylphenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl, N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen, sulfur, phosphorous, or boron such as 2-furyl, 2-thienyl, 2-benzimidazolyloxy or 2-benzothiazolyl; quaternary ammonium, such as triethylammonium; quaternary phosphonium, such as triphenylphosphonium; and silyloxy, such as trimethylsilyloxy.

If desired, the substituents may themselves be further substituted one or more times with the described substituent groups. The particular substituents used may be selected by those skilled in the art to attain the desired desirable properties for a specific application and can include, for example, electron-withdrawing groups, electron-donating groups, and steric groups. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

The entire contents of the patents and other publications referred to in this specification are incorporated herein by reference.

EXAMPLES

Sample 1 (Invention, YD-1)

The invention is exemplified in scheme 1 to prepare compound, YD-1:

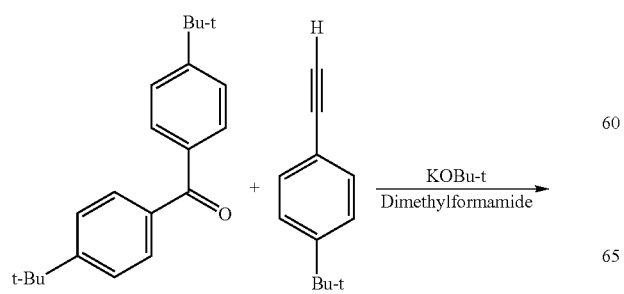

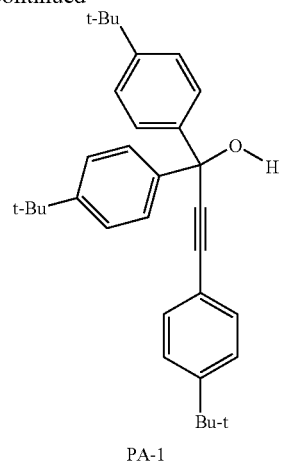

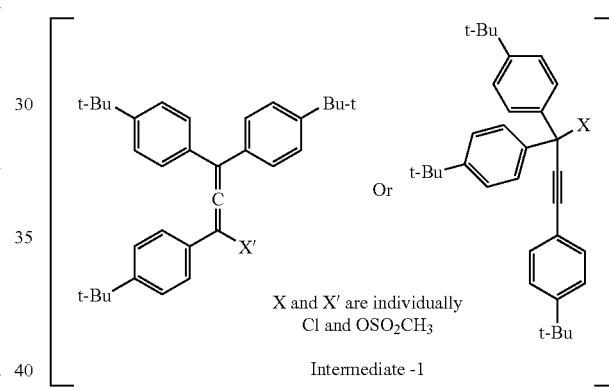

Preparation of the propargyl alcohol, PA-1: Under a nitrogen atmosphere, 4-t-butylphenylacetylene (39.6 g, 250 mMole), was dissolved in dimethylformamide (DMF) (400 mL), stirred with a mechanical stirrer and the solution cool to −10° C. to 0° C. Powdered potassium t-butoxide (KBu'O) (34 g of 95%, 300 mMole), was added over a 10-minute period and the mixture stirred well for approximately 15 minutes at −10° C. to 0° C. To this mixture was then added 4, 4'-di-tert-butylbenzophenone (70.1 g, 238 mMole) all at once. Stirring was continued at −10° C. to 0° C. for approximately 1 hour and then allowed to come to room temperature over a 1-hour period. At the end of this time the solution was cooled to 0° C. and the reaction treated with saturated sodium chloride (100 mL), keeping the temperature below 10° C. The mixture was then diluted with ethyl acetate, washed with 2N—HCl (3×100 mL), dried over MgSO$_4$, filtered and concentrated under reduced pressure. While some solvent was still present, the semi-solid was triturated (500 mL) to give the product as an off-white solid. Yield of propagyl alcohol PA-1, 82 g.

Preparation of Naphthacene Compound, YD-1: Propargyl alcohol PA-1, (40 g, 88 mMole) was dissolved in toluene (300 mL), with slight heating to get complete dissolution, cooled and stirred at 0° C. under a nitrogen atmosphere. To this solution was added triethylamine (NEt$_3$), (12.52 g, 16.05 mL, 123 mMole) and then treated drop-by-drop with methanesulfonyl chloride (CH$_3$SO$_2$Cl), (15.8 g, 110.68 mL 123 mMole), keeping the temperature of the reaction below 10° C. After the addition, the solution was stirred at 0° C. for 15 minutes and then at room temperature for 15 minutes. To the reaction mixture was then added finely powered anhydrous K$_2$CO$_3$ (24.3 g, 176 mMole) and then heated, with good stirring, to 110° C. for 4 hours. After this period, the reaction was cooled, diluted with ethyl acetate (100 mL) and carefully washed with 2N—HCl until acidic. The ethyl acetate solution was dried over MgSO$_4$, filtered and concentrated to give an oil. This oil was dissolved in ether (100 mL) and slowly treated with methanol (100 mL). On standing the naphthacene compound, YD-1 crystallized out, was filtered off and washed with a small volume of methanol and dried. Yield, YD-1, 14 g.

Sample 2 (Inventive, YD-2)

The invention is further exemplified in the following scheme to prepare compound, YD-2:

Scheme 2

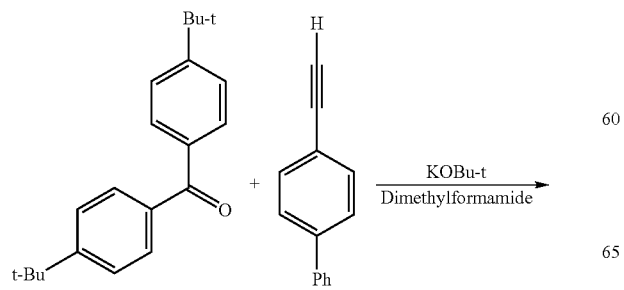

-continued

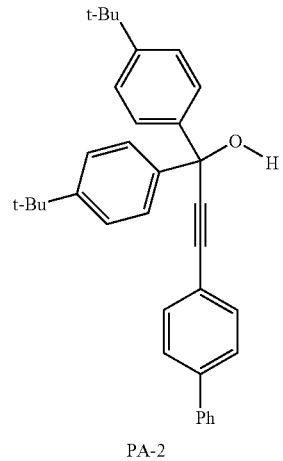

PA-2

CH$_3$SO$_2$Cl/PhCH$_3$/N(C$_2$H$_5$)$_3$

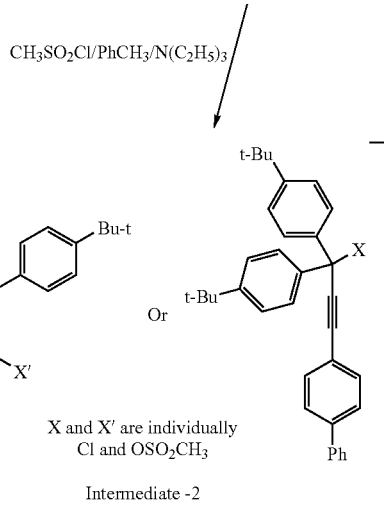

X and X' are individually Cl and OSO$_2$CH$_3$

Intermediate -2

Heat/Inorganic Base

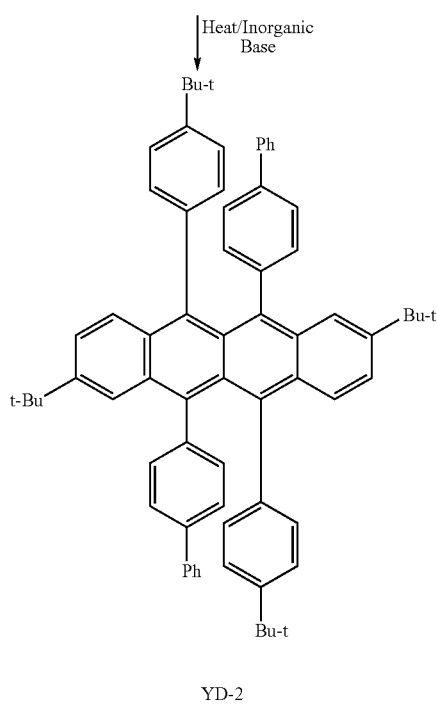

YD-2

Preparation of the propargyl alcohol, PA-2: Under a nitrogen atmosphere, 4-biphenylacetylene (32.76 g of 97%, 178.31 mMole), was dissolved in dimethylformamide (DMF) (750 mL), stirred with a mechanical stirrer and the solution cool to −10° C. to 0° C. Powdered potassium t-butoxide (KBu$^t$O) (25 g of 95%, 213.97 mMole), was added over a 10-minute period and the mixture stirred well for approximately 15 minutes at −10° C. to 0° C. To this mixture was then added 4,4'-di-tert-butylbenzophenone (50 g, 169.81 mMole) all at once. Stirring was continued at −10° C. to 0° C. for approximately 1 hour and then allowed to come to room temperature over a 1-hour period. At the end of this time the solution was cooled to 0° C. and the reaction treated with saturated sodium chloride (100 mL), keeping the temperature below 10° C. The mixture was then diluted with ethyl acetate, washed with 2N—HCl (3×100 mL), dried over MgSO$_4$, treated with decolorizing charcoal (×2), filtered and concentrated under reduced pressure. The crude product was triturated with ether (200 mL) and heptane (500 mL) to give the product as an off-white solid. Yield of propagyl alcohol PA-2, 72 g.

Preparation of Naphthacene Compound, YD-2: Propargyl alcohol PA-2, (5.0 g, 10 mMole) was dissolved in toluene (70 mL), with slight heating to get complete dissolution, cooled and stirred at 0° C. under a nitrogen atmosphere. To this solution was added triethylamine (NEt$_3$), (1.41 g, 1.81 mL, 14 mMole) and then treated drop-by-drop with methanesulfonyl chloride (CH$_3$SO$_2$Cl), (1.79 g, 1.21 mL 14 mMole), keeping the temperature of the reaction below 10° C. After the addition, the solution was stirred at 0° C. for 15 minutes and then at room temperature for 15 minutes. To the reaction mixture was then added finely powered anhydrous Na$_2$CO$_3$ (2.11 g, 20 mMole) and then heated, with good stirring, to 110° C. for 4 hours. After this period, the reaction was cooled, diluted with ethyl acetate (100 mL) and carefully washed with 2N—HCl until acidic. On standing, the product crystallized out. It was filtered off, washed well with methanol and dried. Yield, YD-2, 6.0 g.

Sample 3 (Inventive, YD-3)

Sample 3 is the naphthacene compound YD-3 of the invention. It is prepared from a symmetrical 1,1-diarylpropargyl alcohol in a similar manner to YD-1 and YD-2.

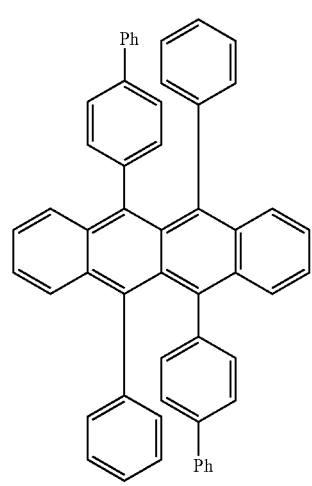

YD-3

Sample 4 (Inventive, YD-4)

Sample 4 is the naphthacene compound YD-4 of the invention. It too is prepared from a symmetrical 1,1-diarylpropargyl alcohol in a similar manner to YD-1 and YD-2

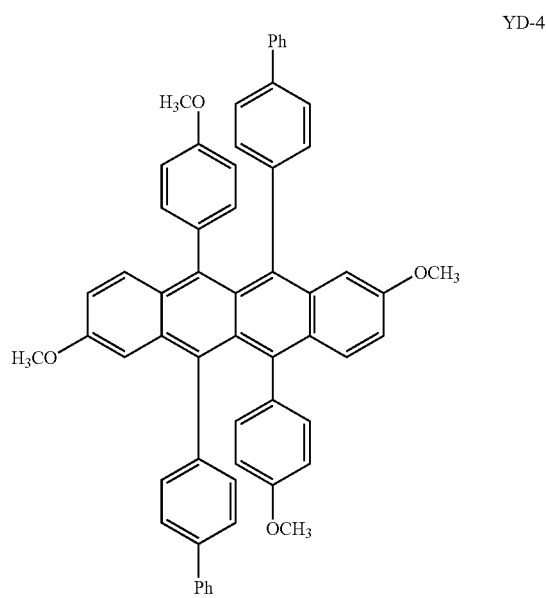

YD-4

Sample 5 (Comparison, Comp-1)

Sample 5 is a comparison employing naphthacene Comp-1. It is Example 4 as described in U.S. Pat. No. 4,855,520 and is prepared from an unsymmetrical 1,1-diarylpropargyl alcohol and produces 3 naphthacene isomers, Comp-1a, Comp-1b and Comp-1c.

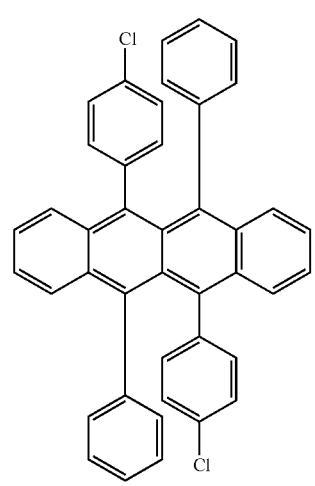

Comp-1a

Comp-1b

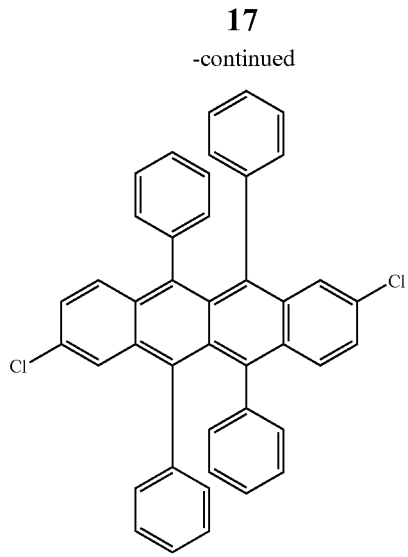

Comp-1c

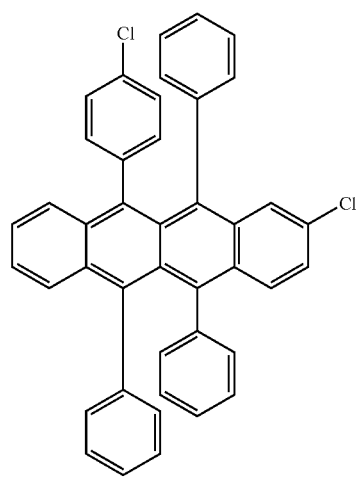

Sample 6 (Comparison, Comp-2)

Sample 3 is another comparison employing naphthacene Comp-2. It is Example 5 as described in U.S. Pat. No. 4,855,520 and is prepared from an unsymmetrical 1,1-diarylpropargyl alcohol and produces 3 naphthacene isomers, Comp-2a, Comp-2b and Comp-2c.

Comp-2a

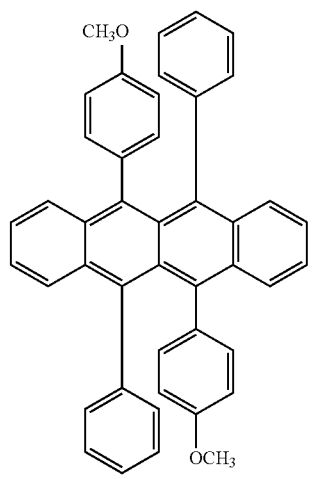

Comp-2b

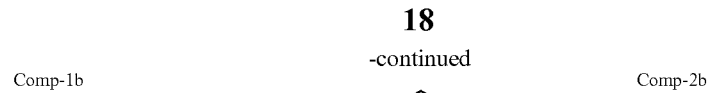

Comp-2c

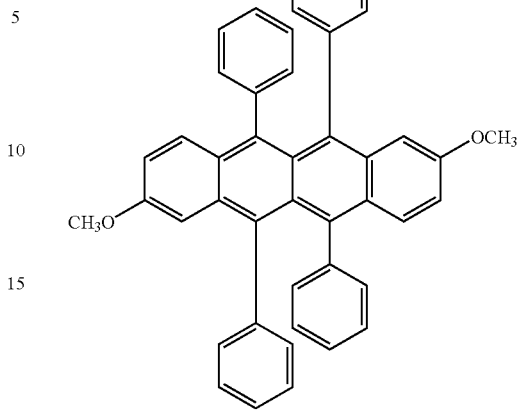

Sample 7 (Comparison, Comp-3)

Sample 7 is a further comparison employing Comp-3. It is an example not specifically described in U.S. Pat. No. 4,855,520, but falls within the scope of U.S. Pat. No. 4,855,520. It is prepared from an unsymmetrical 1,1-diarylpropargyl alcohol and produces 3 naphthacene isomers, Comp-3a, Comp-3b and Comp-3c.

Comp-3a

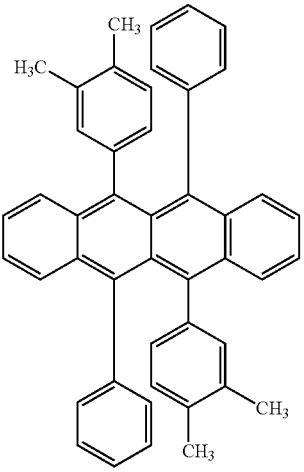

-continued

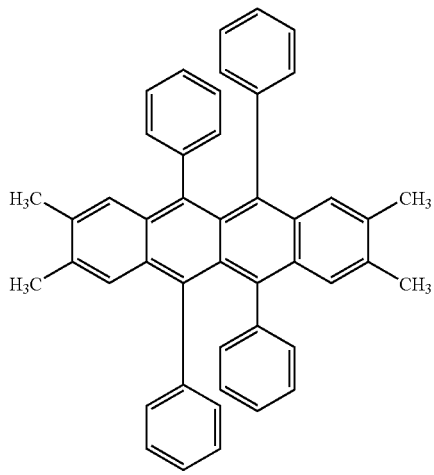
Comp-3b

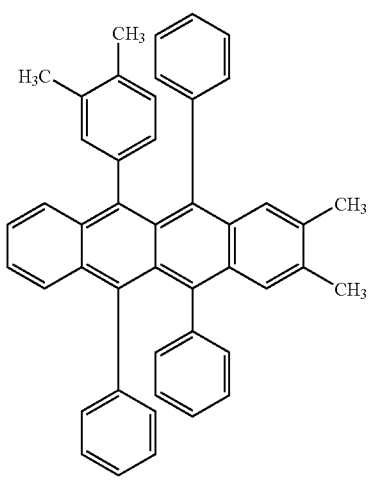
Comp-3c

TABLE 1

| Sample No. | Sample Type | Naphthacene Compound(s) formed | Number of Isomers |
|---|---|---|---|
| 1 | Inventive | YD-1 | 1 |
| 2 | Inventive | YD-2 | 1 |
| 3 | Inventive | YD-3 | 1 |
| 4 | Inventive | YD-4 | 1 |
| 5 | Comparative | Comp-1a | 3 |
| | | Comp-1b | |
| | | Comp-1c | |
| 6 | Comparative | Comp-2a | 3 |
| | | Comp-2b | |
| | | Comp-2c | |
| 7 | Comparative | Comp-3a | 3 |
| | | Comp-3b | |
| | | Comp-3c | |

The number(s) of isomeric naphthacene compounds formed in Samples 1-7 from the different 1,1-diarylpropargyl alcohols were determined by HPLC/MS analysis.

As can be seen from Table 1, the naphthacenes of the invention YD-1 through YD-4 of Samples 1-4 all show the formation of a single isomer when a symmetrically substituted 1,1-diarylpropargyl alcohol as in step (a) of the invention is employed. Whereas, the comparison naphthacenes of U.S. Pat. No. 4,855,520, YD-5-YD-7 of Samples 5-7 each show the formation of three isomeric naphthacenes; Comp-1a through Comp-1c, Comp-2a through Comp-2c and Comp-3a through Comp-3c. Since the naphthacenes of the invention are single isomers they require no separation before use in EL devices whereas, the comparison naphthacenes each form three isomers and require separation into their components before they can be used in EL devices. Symmetrical 1,1-diarylpropargyl alcohols used in step (a) of the current invention unexpectedly give a single naphthacene isomer useful in EL devices to give superior performance.

Embodiments of the invention provide a short, simple, environmentally friendly procedure, without the formation of mixtures of isomers, and can be applied to naphthacenes with a variety of substituents. Such high purity naphthacenes are useful in high performing EL devices.

The invention has been described in detail with particular reference to certain preferred embodiments thereof, but it will be understood that variations and modifications can be effected within the spirit and scope of the invention.

The patents and other publications referred to are incorporated herein in their entirety.

What is claimed is:

1. A process for synthesizing a single isomer of a naphthacene compound comprising the steps of:
   (a) reacting a symmetrically substituted 1,1-diarylpropargyl alcohol compound with a reagent capable of forming a leaving group to form a reaction mixture containing a intermediate;
   and then
   (b) heating the intermediate in the presence of a solvent and in the absence of any oxidizing agent to form a single naphthacene compound.

2. A process of claim 1 wherein an acid scavenger is present in step (a).

3. A process of claim 2 wherein said acid scavenger is an amine.

4. A process of claim 2 wherein said acid scavenger is triethylamine.

5. A process of claim 2 wherein said acid scavenger is an inorganic base.

6. A process of claim 1 wherein a base is present in step (b).

7. A process of claim 6 wherein said base is an amine.

8. A process of claim 6 wherein said base is triethylamine.

9. A process of claim 6 wherein said base is an inorganic base.

10. A process of claim 9 wherein said inorganic base is the basic salt of a metal.

11. A process of claim 9 wherein said inorganic base is the basic salt of a metal from groups 1 and 2 of the periodic table.

12. A process of claim 9 wherein said inorganic base is a metal or non-metal carbonate.

13. A process of claim 9 wherein said inorganic base comprises one selected from $Li_2CO_3$, $Na_2CO_3$, $K_2CO_3$, $Rb_2CO_3$, $Cs_2CO_3$, $MgCO_3$, $CaCO_3$, $BaCO_3$, sodium acetate (NaOAc), and $(NH_4)_2CO_3$.

14. A process of claim 1 wherein steps (a) and (b) employ solvents that are different.

15. A process of claim 14 wherein the solvent in step (a) is selected from diethyl ether, methylene chloride, ethyl acetate and tetrahydrofuran.

16. A process of claim 14 wherein the solvent in step (b) is selected from benzene, toluene, xylene and xylene mixtures.

17. A process of claim 1 wherein steps (a) and (b) employ solvents that are the same.

18. A process of claim 17 wherein the solvent is the same for both steps (a) and (b) and is selected from benzene, toluene and xylenes.

19. A process of claim 1 wherein the reaction temperature in step (a) is in the range from –30° C. to +30° C.

20. A process of claim 19 wherein the reaction temperature in step (a) is in the range from 0° C. to +20° C.

21. A process of claim 1 wherein the reaction temperature in step (b) is in the range from +30° C. to +180° C.

22. A process of claim 21 wherein the reaction temperature in step (b) is in the range from +70° C. to +120° C.

23. A process of claim 1 wherein the reagent capable of forming the leaving group comprises one selected from thionyl chloride, thionyl bromide, phosphorous pentachloride, phosphorous trichloride, phosphorous tribromide, phosphorous oxychloride, acetyl chloride, and alkanesulfonyl chlorides.

24. A process of claim 1 wherein the reagent capable of forming the leaving group comprises one from thionyl chloride, phosphorous trichloride, and methanesulfonyl chloride.

25. A process of claim 1 wherein said intermediate of step (a) is represented by Formula (Ia):

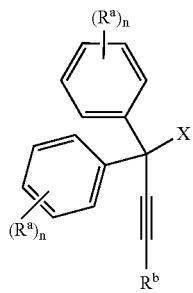

(Ia)

wherein:
the $R^a$ groups are selected from hydrogen or substituent groups;
$R^b$ is hydrogen or a substituent group;
n is selected from 0-4;
X is a leaving group; and
provided that when n is 0 $R^b$ is not phenyl.

26. A process of claim 1 wherein said intermediate of step (a) is represented by Formula (IIa):

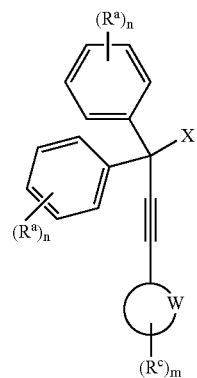

(IIa)

wherein:
the $R^a$ and $R^c$ groups are selected from hydrogen or substituent groups;
n is selected from 0-4;
m is selected from 0-5;
W represents the atoms necessary to complete a heterocyclic or carbocyclic ring group;
X is a leaving group; and
provided that when W forms a phenyl group the $R^a$ and $R^c$ are not all hydrogen.

27. A process of claim 1 wherein said intermediate of step (a) is represented by Formula (IIIa):

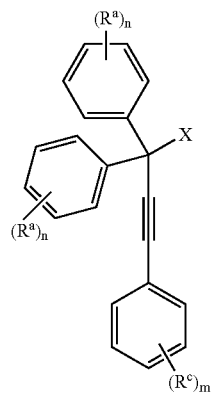

(IIIa)

wherein:
the $R^a$ groups are selected from hydrogen or substituent groups;
$R^c$ is hydrogen or a substituent group;
n is selected from 0-4;
m is selected from 0-5;
X is a leaving group; and
provided that $R^a$ and $R^c$ are not all hydrogen.

28. A process of claim 1 wherein said intermediate of step (a) is represented by Formula (Ib):

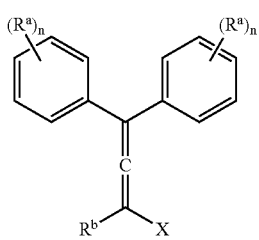

(Ib)

wherein:

the $R^a$ and $R^b$ groups are selected from hydrogen or substituent groups;

n is selected from 0-4;

X is a leaving group; and provided that when $R^b$ is a phenyl group the $R^a$ groups are not hydrogen.

29. A process of claim 1 wherein said intermediate of step (a) is represented by Formula (IIb):

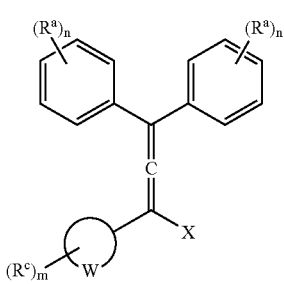

(IIb)

wherein:

the $R^a$ and $R^c$ groups are selected from hydrogen or substituent groups;

n is selected from 0-4;

m is selected from 0-5;

W represents the atoms necessary to complete a heterocyclic or carbocyclic ring group;

X is a leaving group; and provided that when W forms a phenyl group the $R^a$ and $R^c$ are not all hydrogen.

30. A process of claim 1 wherein said intermediate of step (a) is represented by Formula (IIIb):

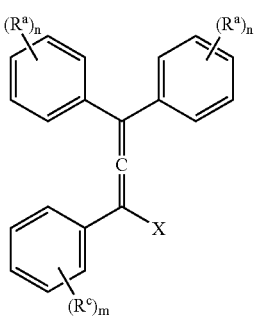

(IIIb)

wherein:

the $R^a$ groups are selected from hydrogen or substituent groups;

$R^c$ is hydrogen or a substituent group;

n is selected from 0-4;

m is selected from 0-5;

X is a leaving group; and provided that $R^a$ and $R^c$ are not all hydrogen.

31. A process of claim 1 wherein said naphthacene compound is represented by Formula (IVa):

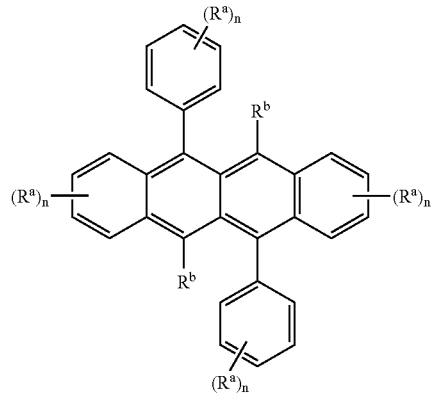

(IVa)

wherein:

$R^a$ and $R^b$ are substituent groups;

n is selected from 0-4; and provided that when n is 0 $R^b$ is not phenyl.

32. A process of claim 1 wherein said naphthacene compound is represented by Formula (IVb):

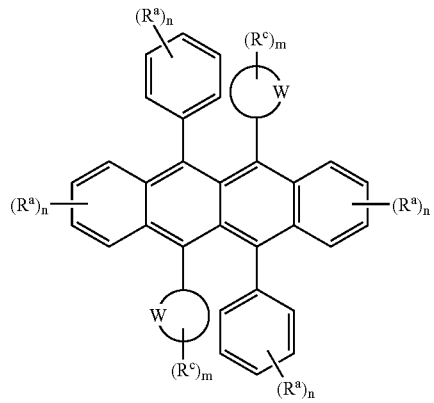

(IVb)

wherein:

the $R^a$ and $R^c$ groups are selected from hydrogen or substituent groups;

n is selected from 0-4;

m is selected from 0-5;

W represents the atoms necessary to complete a heterocyclic or carbocyclic ring group; and provided that when W forms a phenyl group the $R^a$ and $R^c$ are not all hydrogen.

33. A process of claim 1 wherein said naphthacene compound is represented by Formula (IVc):

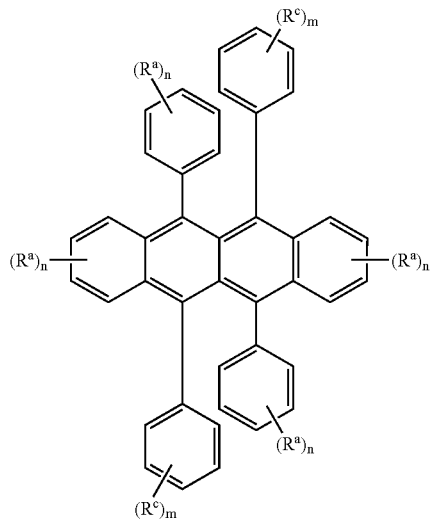

(IVc)

wherein:
the $R^a$ groups are selected from hydrogen or substituent groups;
$R^c$ is hydrogen or a substituent group;
n is selected from 0-4;
m is selected from 0-5; and
provided that $R^a$ and $R^c$ are not all hydrogen.

34. A process of claim 1 wherein said symmetrically substituted 1,1-diarylpropargyl alcohol compound is represented by Formula (Va):

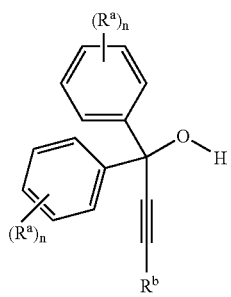

(Va)

wherein:
$R^a$ and $R^b$ are substituent groups;
n is selected from 0-4; and
provided that when n is 0 $R^b$ is not phenyl.

35. A process of claim 1 wherein said symmetrically substituted 1,1-diarylpropargyl alcohol is represented by Formula (Vb):

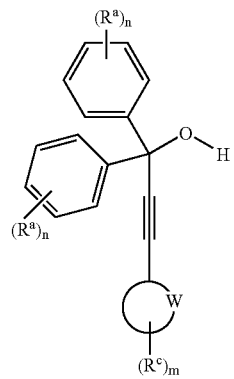

(Vb)

wherein:
the $R^a$ and $R^c$ groups are selected from hydrogen or substituent groups;
n is selected from 0-4;
m is selected from 0-5;
W represents the atoms necessary to complete a heterocyclic or carbocyclic ring group; and
provided that when W forms a phenyl group the $R^a$ and $R^c$ are not all hydrogen.

36. A process of claim 1 wherein said symmetrically substituted 1,1-diarylpropargyl alcohol is represented by Formula (Vc):

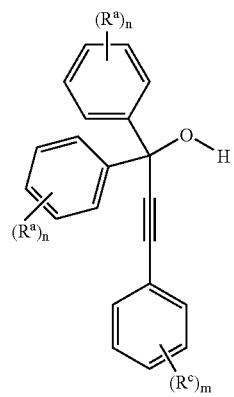

(Vc)

wherein:
the $R^a$ and $R^c$ groups are selected from hydrogen or substituent groups;
n is selected from 0-4;
m is selected from 0-5; and
provided that $R^a$ and $R^c$ are not all hydrogen.

37. A process of claim 25 wherein X is selected from Cl, Br, acetate(OAc), alkanesulfonate, and phosphate.

38. A process of claim 28 wherein X is selected from Cl, Br, acetate(OAc), alkanesulfonate, and phosphate.

39. A process of claim 25 wherein X is selected from Cl and methanesulfonate($CH_3SO_3$).

40. A process of claim 28 wherein X is selected from Cl and methanesulfonate($CH_3SO_3$).

41. A process of claim 27 wherein either of n or m is at least one, and $R^a$ and $R^c$ are individually selected from hydrogen, cyano, nitro, halogen, hydroxy, alkyl, alkenyl, alkoxy, aryl, aryloxy, acyl, oxysulfonyl, acyloxy, oxycarbonyl, carboxy, sulfoxide, thio, sulfamoyl, sulfonamido, sulfonyl, carbamoyl, carbonamido, ureido, and trifluoromethyl groups.

42. A process of claim 30 wherein either of n or m is at least one, and $R^a$ and $R^c$ are individually selected from hydrogen, cyano, nitro, halogen, hydroxy, alkyl, alkenyl, alkoxy, aryl, aryloxy, acyl, oxysulfonyl, acyloxy, oxycarbonyl, carboxy, sulfoxide, thio, sulfamoyl, sulfonamido, sulfonyl, carbamoyl, carbonamido, ureido, and trifluoromethyl groups.

43. A process of claim 27 wherein $R^a$ and $R^c$ individually can form a carbocyclic or heterocyclic ring.

44. A process of claim 27 wherein $R^a$ and $R^c$ individually can form an aryl ring.

45. A process of claim 27 wherein $R^a$ and $R^c$ individually can form a furyl, imidazolyl, pyrazolyl, pyridyl, pyrrolyl, thienyl, or triazolyl ring.

46. A process of claim 30 wherein $R^a$ and $R^c$ individually can form a carbocyclic or heterocyclic ring.

47. A process of claim 30 wherein $R^a$ and $R^c$ individually can form an aryl ring.

48. A process of claim 30 wherein $R^a$ and $R^c$ individually can form a furyl, imidazolyl, pyrazolyl, pyridyl, pyrrolyl, thienyl, or triazolyl ring.

49. A process of claim 33 wherein an acid scavenger is present in step (a).

50. A process of claim 49 wherein said acid scavenger is an amine.

51. A process of claim 33 wherein a base is present in step (b).

52. A process of claim 51 wherein said base is the basic salt of a metal from groups 1 and 2 of the periodic table.

53. A process of claim 51 wherein said base is a metal or non-metal carbonate.

54. A process of claim 33 wherein the solvents in steps (a) and (b) are different.

55. A process of claim 33 wherein the solvents in steps (a) and (b) are the same.

56. A process of claim 33 wherein the temperature in step (a) is in the range from −30° C. to +30° C.

57. A process of claim 33 wherein the temperature in step (b) is in the range from +30° C. to +180° C.

58. A process of claim 33 wherein the reagent capable of forming the leaving group comprises one selected from thionyl chloride, thionyl bromide, phosphorous pentachloride, phosphorous trichloride, phosphorous tribromide, phosphorous oxychloride, acetyl chloride, and alkanesulfonyl chlorides.

59. A process of claim 1 wherein step (b) is subjected to an inert atmosphere.

60. A process of claim 33 wherein step (b) is subjected to an inert atmosphere.

61. A process of claim 1 wherein the reaction time of step (a) is from 5 minutes to 3 hours.

62. A process of claim 1 wherein the reaction time of step (a) is from 10 minutes to 30 minutes.

63. A process of claim 1 wherein the reaction mixture of step (b) is heated from 1 to 48 hours.

64. A process of claim 1 wherein the reaction mixture of step (b) is heated from 1 to 8 hours.

65. A process of claim 1 wherein the reaction mixture of step (b) is heated from 4 to 5 hours.

* * * * *